United States Patent
Monro et al.

(10) Patent No.: US 8,338,799 B2
(45) Date of Patent: Dec. 25, 2012

(54) OPTICAL FIBER SENSOR

(75) Inventors: Tanya Monro, Adelaide (AU); Heike Ebendorff-Heidepriem, Dover Gardens (AU); Stephen Warren Smith, Morris (AU); Shahraam Afshar Vahid, Magill (AU); Yinlan Ruan, Paradise (AU)

(73) Assignee: Adelaide Research & Innovation Pty Ltd., Adelaide (AU)

( * ) Notice: Subject to any disclaimer, the term of this patent is extended or adjusted under 35 U.S.C. 154(b) by 277 days.

(21) Appl. No.: 12/670,034

(22) PCT Filed: Jul. 24, 2008

(86) PCT No.: PCT/AU2008/001073
§ 371 (c)(1),
(2), (4) Date: Jun. 7, 2010

(87) PCT Pub. No.: WO2009/012528
PCT Pub. Date: Jan. 29, 2009

(65) Prior Publication Data
US 2010/0237255 A1 Sep. 23, 2010

Related U.S. Application Data

(60) Provisional application No. 60/951,553, filed on Jul. 24, 2007, provisional application No. 60/952,063, filed on Jul. 26, 2007.

(51) Int. Cl.
*G01J 1/58* (2006.01)
*G02B 6/036* (2006.01)
(52) U.S. Cl. .............. 250/458.1; 250/459.1; 385/126
(58) Field of Classification Search .......... 250/458.1, 250/459.1; 385/123, 125, 126, 127, 128
See application file for complete search history.

(56) References Cited

U.S. PATENT DOCUMENTS

| | | | |
|---|---|---|---|
| 6,358,748 B1 | 3/2002 | Weiss |
| 6,385,380 B1 | 5/2002 | Friedrich et al. |
| 6,445,861 B1 | 9/2002 | Shaw et al. |
| 6,496,634 B1 | 12/2002 | Levenson |
| 6,661,957 B1 | 12/2003 | Levenson et al. |
| 6,845,203 B1 | 1/2005 | Levenson |
| 6,993,230 B2 | 1/2006 | Sanghera et al. |

(Continued)

FOREIGN PATENT DOCUMENTS

JP 2007/009094 1/2007

(Continued)

OTHER PUBLICATIONS

Afshar et al., "Enhancement of fluorescence-based sensing using microstructured optical fibers", Optics Express, 15, 2007, pp. 17891-17901.

(Continued)

*Primary Examiner* — Mark R Gaworecki
(74) *Attorney, Agent, or Firm* — Greenblum & Bernstein, P.L.C.

(57) ABSTRACT

A sensor based on optical fiber technology is described. The sensor includes an elongate core for propagating light having an excitation wavelength; an interaction region that includes a fluorescent material for excitation by the propagated light to produce fluorescent light; and an interface region defining a boundary between the elongate core and the interaction region. The elongate core of the sensor is adapted to increase an intensity of the propagated light at the interface region to increase the amount of captured fluorescent light in the elongate core.

30 Claims, 13 Drawing Sheets

U.S. PATENT DOCUMENTS

| | | | |
|---|---|---|---|
| 7,054,513 B2 | 5/2006 | Herz et al. | |
| 7,142,758 B1 | 11/2006 | Herz et al. | |
| 7,295,740 B2 | 11/2007 | Sanghera et al. | |
| 7,362,938 B1 | 4/2008 | Herz et al. | |
| 2005/0025965 A1 | 2/2005 | Sanghera et al. | |
| 2005/0074215 A1 | 4/2005 | Sanghera et al. | |
| 2005/0111805 A1* | 5/2005 | Hertz et al. | 385/125 |
| 2006/0230792 A1 | 10/2006 | Sanghera et al. | |
| 2006/0257088 A1 | 11/2006 | Herz et al. | |
| 2007/0110377 A1 | 5/2007 | Sanghera et al. | |
| 2007/0140638 A1 | 6/2007 | Yang et al. | |
| 2008/0060387 A1 | 3/2008 | Sanghera et al. | |
| 2008/0085086 A1 | 4/2008 | Herz et al. | |

FOREIGN PATENT DOCUMENTS

| | | |
|---|---|---|
| WO | 02/16971 | 2/2002 |
| WO | 2007/041791 | 4/2007 |
| WO | 2007/041792 | 4/2007 |

OTHER PUBLICATIONS

Ruan et al., "Detection of quantum-dot labeled proteins using soft glass microstructured optical fibers", Optics Express, 15, 2007, pp. 17819-17826.

Afshar et al., "Enhanced fluorescence sensing using microstructued optical fibers: a comparison of forward and backward collection modes", Optics Letters, 33, 2008, pp. 1473-1475.

Afshar et al., "Highly efficient fluorescence sensing using microstructured optical fibers; general model and experiment", 19th International Conference on Optical Fibre Sensors, Perth, Australia, Apr. 14-18, 2008 Proceedings of SPIE, 7004, 2008, pp. 149.

Warren-Smith et al., "Highly-efficient fluorescence sensing using microstructured optical fibers; side-access and thin-layer configurations", 19th International Conference on Optical Fibre Sensors, Perth, Australia, Apr. 14-18, 2008, Proceedings of SPIE, 7004, 2008, pp. 99.

Monro et al., "Antibody immobilization within glass microstructured fibers: a route to sensitive and selective biosensors", 19th International Conference on Optical Fibre Sensors, Perth, Australia, Apr. 14-18, 2008, Proceedings of SPIE, 7004, (Post Deadline Paper), 2008.

Warren-Smith et al., "Theoretical study of liquid-immersed exposed-core microstructured optical fibers for sensing", Optics Express, 16, 12, 2008, pp. 9034-9045.

Schartner et al., "An optical fibre protein sensor", Optical Internet, 2007 and the 2007 32nd Australian Conference on Optical Fibre Technology Joint International Conference on, IEEE, Piscataway, NJ, USA, pp. 1-3.

Hoo Y L et al., "Design and modeling of a photonic crystal fiber gas sensor", Applied Optics, vol. 42, No. 18, Jun. 20, 2003, pp. 3509-3515.

Lars Rindorf et al., "Towards biochips using microstructured optical fiber sensors", Analytical and Bioanalytical Chemistry, Springer, Berlin, vol. 385, No. 8, Jun. 8, 2006, pp. 1370-1375.

Wiederhecker et al., "Field enhancement within an optical fibre with a subwavelength air core", Nature Photonics 1, 2007, pp. 115-118.

Monro, "Optical fibres: Beyond the diffraction limit", Nature Photonics 1, 2007, pp. 89-90.

Search report from E.P.O., mail date is Sep. 17, 2010.

* cited by examiner

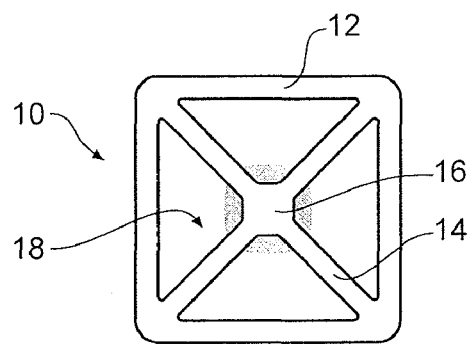
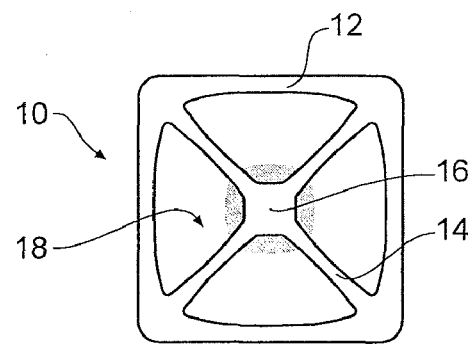
Fig 14A  Fig 14B
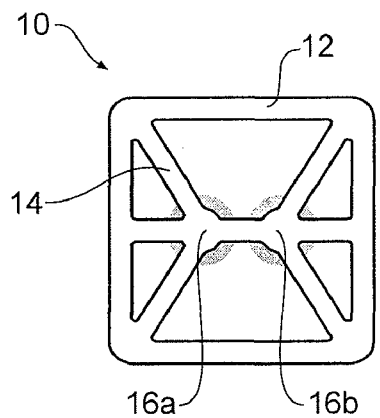
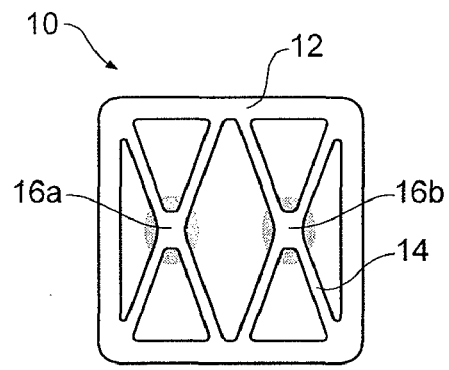
Fig 14C  Fig 14D
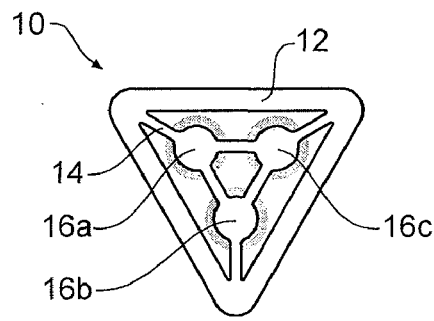
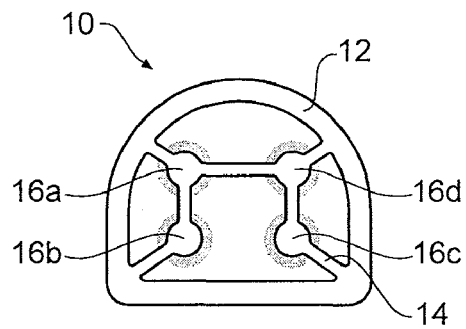
Fig 14E  Fig 14F

OPTICAL FIBER SENSOR

PRIORITY

The present application claims priority from U.S. Provisional Patent Application No. 60/951,553 entitled "OPTICAL FIBER SENSOR", filed on 24 Jul. 2007 and U.S. Provisional Patent Application No. 60/952,063 entitled "OPTICAL FIBER SENSOR", filed on 26 Jul. 2007.

The entire content of each of these applications is hereby incorporated by reference.

REFERENCE TO CO-PENDING APPLICATIONS FOR PATENT

The present invention is related to the following applications for patent:

PCT Publication No. WO2007/041792 entitled "FABRICATION OF NANOWIRES", filed 12 Oct. 2006.

PCT Publication No. WO 2007/041791 entitled "METHOD AND DEVICE FOR FORMING MICROSTRUCTURED FIBRE", filed 12 Oct. 2006.

The entire content of each of these applications is hereby incorporated by reference.

TECHNICAL FIELD

The present invention relates to optical sensing. In a particular form the present invention relates to a fluorescence type sensor based on optical fiber technology.

INCORPORATION BY REFERENCE

The entire content of each of the following documents is hereby incorporated by reference.

Rost, F. W. D., *Fluorescent Microscopy*, Cambridge University Press, Cambridge, UK, (1992).

Snyder, A. W. and Love, J. D., *Optical Waveguide Theory*, Chapman and Hall, 2-6 Boundary Row, London SE1 8HN, UK, (1995).

Marcuse, D., *Journal of Lightwave Technology*, 6, 1273-1279 (1988).

Washburn, E. W., *Physical Review*, 17, 273-283 (1921).

Agrawal, P., *Nonlinear Fiber Optics*, Academic Press, (2007).

Afshar, V. S., Warren-Smith, S. C., Monro, T. M., "Enhancement of fluorescence-based sensing using microstructured optical fibres", *Optics Express*, 15, 17891-17901 (2007).

Ruan, Y., Schartner, E. P., Ebendorf-Heidepriem, H., Hoffman, P., Monro, T. M., "Detection of quantum-dot labeled proteins using soft glass microstructured optical fibers", *Optics Express*, 15, 17819-17826 (2007).

Afshar, V. S., Ruan, Y., Warren-Smith, S. C., Monro, T. M., "Enhanced fluorescence sensing using microstructured optical fibers: a comparison of forward and backward collection modes", *Optics Letters*, 33, 1473-1475 (2008).

Afshar, V. S., Ruan, Y., Warren-Smith, S. C., Ebendorf-Heidepriem, H., Monro, T. M., "Highly efficient fluorescence sensing using microstructured optical fibers; general model and experiment", 19th International Conference on Optical Fibre Sensors, Perth, Australia, Apr. 14-18, 2008 *Proceedings of SPIE*, 7004, 149 (2008).

Warren-Smith, S. C., Afshar, V. S., Monro, T. M., "Highly-efficient fluorescence sensing using microstructured optical fibers; side-access and thin-layer configurations", 19th International Conference on Optical Fibre Sensors, Perth, Australia, Apr. 14-18, 2008 *Proceedings of SPIE*, 7004, 99 (2008).

Monro, T. M., Ruan, Y., Ebendorf-Heidepriem, H., Foo, H., Hoffman, P., Moore, R. C., "Antibody immobilization within glass microstructured fibers: a route to sensitive and selective biosensors", 19th International Conference on Optical Fibre Sensors, Perth, Australia, Apr. 14-18, 2008, *Proceedings of SPIE*, 7004, (Post Deadline Paper) (2008)

Warren-Smith, S. C., Afshar, V. S., Monro, T. M., "Theoretical study of liquid-immersed exposed-core microstructured optical fibers for sensing", *Optics Express*, 16, 12, 9034-9045 (2008).

BACKGROUND

Optical sensing devices can be utilized to detect small concentrations of chemicals or biological materials, and thus have many applications in the areas of pollution control, defense, corrosion detection, explosives detection, water quality monitoring, biological sensing and quality control in manufacturing. There have been a number of attempts to create a sensing device based on optical fiber technology employing the principles of absorption and fluorescence spectroscopy. As would be appreciated by those skilled in the art, the sensitivity of such an optical fiber based device is primarily related to the power fraction of the guided mode field that is available to be overlapped with the material to be sensed.

Depending on the structure or geometrical configuration of the fiber based sensor, the fraction of the guided light that is available for material interactions can vary widely. A number of attempts at developing a fiber based sensor have made use of the evanescent tails of the modal field (evanescent sensing) or alternatively the central portion of a mode guided within an air core. Some examples of fiber-based sensors that utilize evanescent based sensing principles include tapered fibers, D-shaped fibers, microstructured optical fibers (MOFs), photonic crystal fibers (PCF) and even nanowires where almost all the mode becomes available for sensing. Other examples of waveguide geometries that can provide access to light-material interactions for sensing that do not necessarily rely on making use of the evanescent field include capillary tubes and hollow core photonic bandgap fibers.

However, each of these categories of fiber-based sensors described above has a number of disadvantages. For non-evanescent sensors, while there is often excellent light matter overlap, there are a number of technical difficulties in implementing a practical sensor. For geometries in which the optical field available for light-matter interactions is located within an air core (such as capillary tubes or hollow core MOF), the requirement for a cladding region to surround this core and thus provide confinement for the mode restricts options for sensing the local environment. A further drawback of these devices is that it is generally necessary to load sensors of the type at their ends.

In contrast, nanowires provide ready external access to the optical field. However, the most significant practical restriction with these devices is related to difficulties in the handling of nanowires due to their small dimensions and the resultant issues with integration, fragility and contamination. While the well-studied case of D-shaped fibers offers a more practical alternative, evanescent field based sensors of this type can offer only relatively small light-matter overlap, and hence low efficiency. A secondary and related disadvantage is that these fibers do not efficiently capture fluorescent photons so that they may be propagated as a fluorescent signal to a location where the signal may be analyzed.

One example of an evanescent type fiber based sensor that attempts to address the capture and propagation of fluorescent photons is illustrated in FIG. 1 which is a MOF sensor 100 that includes a central core region 110 for propagation of light having an excitation wavelength 130 surrounded by three longitudinally extending elongate channels or chambers 120, 121, 122. In this example, channel 121 is filled with a fluorescent material 140 within solution which on excitation by a portion of light of excitation wavelength 130 arising from the evanescent field of light propagating along central core region 110 will cause fluorescence 145 of light of fluorescent wavelength 131 which radiates substantially uniformly in all directions. A component of this fluorescence 145 is then captured by central core region 110 and then propagated along MOF sensor 100 for detection either by reflection at a proximal end 150 or by transmission at a distal end 160 of MOF sensor 100.

Whilst a MOF sensor of this type has many convenient features such as ease of filling, close to real time measurements and deployment as they may be readily connected to conventional fiber based systems, in practice the relatively low light matter overlap and the associated low capture efficiency of the fluorescent photons in central core region 110 has meant that MOF sensors of this configuration have only been able to demonstrate relatively low sensitivities.

Accordingly, there is a need for an optical fiber based sensor utilizing fluorescence that is capable of providing increased sensitivity that is readily deployable.

SUMMARY

In a first aspect the present invention accordingly provides a sensor including:

an elongate core for propagating light having an excitation wavelength;

an interaction region that includes a fluorescent material for excitation by the propagated light to produce fluorescent light; and an interface region located between the elongate core and the interaction region; wherein the elongate core is adapted to increase an intensity of the propagated light at the interface region to increase the amount of captured fluorescent light in the elongate core.

In an embodiment the elongate core is adapted to increase the intensity of the guided light at the interface region by having a cross sectional dimension less than or of the same order as the excitation wavelength.

In an embodiment the elongate core is adapted to increase an intensity of the guided light at the interface region by selecting the elongate core to have a refractive index greater than that of the interaction region.

In an embodiment a difference in refractive index between the elongate core and the interaction region is greater than 0.3.

In an embodiment the difference in refractive index between the elongate core and the interaction region is greater than 0.6.

In an embodiment the difference in refractive index between the elongate core and the interaction region is greater than 1.0.

In an embodiment the captured fluorescent light is propagated along the elongate core.

In an embodiment the interaction region extends longitudinally along the elongate core.

In an embodiment the elongate core is a nanowire supported by a support structure that defines the interaction region.

In an embodiment the support structure attaches the elongate core to a supportive outer jacket.

In an embodiment the intensity of the propagated light at the interface region is greater than an intensity of the propagated light within the elongate core.

In an embodiment the intensity of the propagated light at the interface region is greater than the intensity of a peak value of the propagated light within the elongate core.

In an embodiment the interaction region is a containment region for containing the fluorescent material in liquid form.

In an embodiment the containment region is fillable from a filling end of the sensor.

In an embodiment the sensor is irradiated with light having the excitation wavelength at an input end of the sensor, the input end opposed to the filling end, and wherein fluorescent light is captured and propagated back towards the input end for detection.

In an embodiment the interface region is exposed.

In an embodiment the interface region is exposed at a plurality of locations along the elongate core.

In an embodiment the interface region includes at least one portion coated with the fluorescent material.

In an embodiment the fluorescent material is a fluorescently labeled antibody for the detection of a predetermined biomolecule.

In a second aspect the present invention accordingly provides a method for sensing including:

propagating light of an excitation wavelength down an elongate core of a sensor, the sensor including an interaction region that includes a fluorescent material;

enhancing an intensity of the propagated light at an interface region relative to an intensity of the propagated light within the elongate core, the interface region located between the elongate core and the interaction region to thereby increase the amount of captured fluorescent light in the elongate core.

In an embodiment the intensity of the propagated light at the interface region is greater than a peak intensity of propagated light within the elongate core.

In an embodiment the step of enhancing includes reducing the cross sectional dimension of the elongate core to less than or of the same order as the excitation wavelength.

In an embodiment the step of enhancing includes selecting the elongate core to have a refractive index substantially greater than that of the interaction region.

In an embodiment the method further includes propagating the captured fluorescent light along the elongate core.

In a third aspect the present invention accordingly provides a sensor including:

a microstructured optical fiber (MOF) including a solid core for propagating light having an excitation wavelength;

an interaction region surrounding or part surrounding the solid core, the interaction region incorporating a fluorescent material for excitation by the propagated light to produce fluorescent light; and an interface region located between the solid core and the interaction region; wherein the solid core is adapted to increase a discontinuity in the electromagnetic field of the propagated light at the interface region, thereby enhancing the intensity of the propagated light at the interface region.

In an embodiment the interface region is coated by a fluorescent material at a plurality of locations spaced along the solid core.

In an embodiment a plurality of different fluorescent materials are coated at the plurality of locations along the solid core.

In an embodiment the interface region is exposed along the solid core.

In an embodiment the interface region is partially exposed at locations corresponding to the plurality of locations where the interface region is coated.

In a fourth aspect the present invention accordingly provides a sensor including:

a microstructured optical fiber (MOF) including a plurality of solid cores for propagating light having an excitation wavelength;

a plurality of interaction regions surrounding or part surrounding a respective solid core and incorporating fluorescent material for excitation by the propagated light to produce fluorescent light; and corresponding interface regions located between each of the interaction regions and the respective solid cores, wherein a selection of the plurality of solid cores are adapted to increase a discontinuity in the electromagnetic field of the propagated light at the corresponding interface region, thereby enhancing the intensity of the propagated light at the corresponding interface region.

In an embodiment the fluorescent material is varied over the plurality of interaction regions.

BRIEF DESCRIPTION OF THE DRAWINGS

Illustrative embodiments of the present invention will be discussed with reference to the accompanying drawings wherein:

FIGS. 14A to 14F are a series of cross-sectional profiles of sensor configurations in accordance with various embodiments of the present invention.

In the following description, like reference characters designate like or corresponding parts throughout the several views of the drawings.

DETAILED DESCRIPTION

The following description contains specific information pertaining to the implementation of the present invention. One skilled in the art will recognize that the present invention may be implemented in a manner different from that specifically discussed in the present application. Moreover, some of the specific details of the invention are not discussed in order not to obscure the invention. The specific details not described in the present application are within the knowledge of a person of ordinary skill in the art.

The drawings in the present application and their accompanying detailed description are directed to merely example embodiments of the invention. To maintain brevity, other embodiments of the invention which use the principles of the invention are not specifically described in the present application and are not specifically illustrated by the present drawings.

Figure 2:
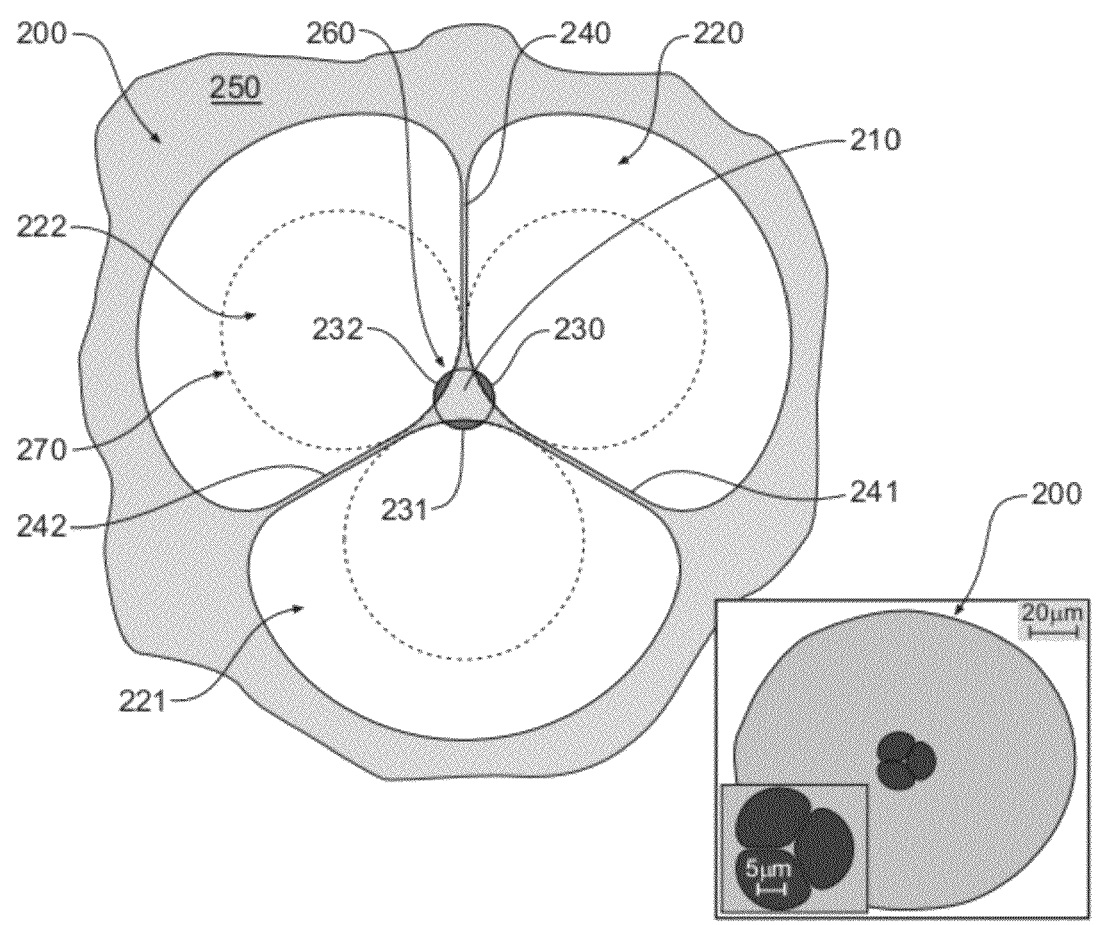
FIG. 2 includes both an enlarged front cross sectional view and a scanning electron microscope (SEM) image of a sensor in accordance with a first illustrative embodiment of the present invention.

Referring now to FIG. 2, there is shown an enlarged front cross sectional view and a SEM image of a sensor 200 in accordance with an illustrative embodiment of the present invention. In this illustrative embodiment, sensor 200 is a MOF and includes an elongate core portion 210 located within a cladding or outer region 250 and supported by a support structure including three equally spaced radial struts 240, 241, 242 extending from outer region 250 to the core portion 210.

Between each pair of opposed radial struts 240-241, 241-242, 242-240 and the outer region 250 there is defined respective longitudinal channels 220, 221, 222 extending along the length of the sensor and which in this embodiment function as an interaction region. In this illustrative embodiment, the diameter d of core portion 210 of sensor 200 is 1.8 μm and is formed of SF57 type glass which is a commercially available Schott lead silicate having a relatively high linear refractive index of 1.84625.

Methods related to the fabrication of sensor 200 are described in PCT Publication No. WO2007/041792 entitled "FABRICATION OF NANOWIRES" and PCT Publication No. WO 2007/041791 entitled "METHOD AND DEVICE FOR FORMING MICROSTRUCTURED FIBRE", both filed 12 Oct. 2006 by the applicant of the present application and incorporated herein by reference in their entirety.

Figure 3:
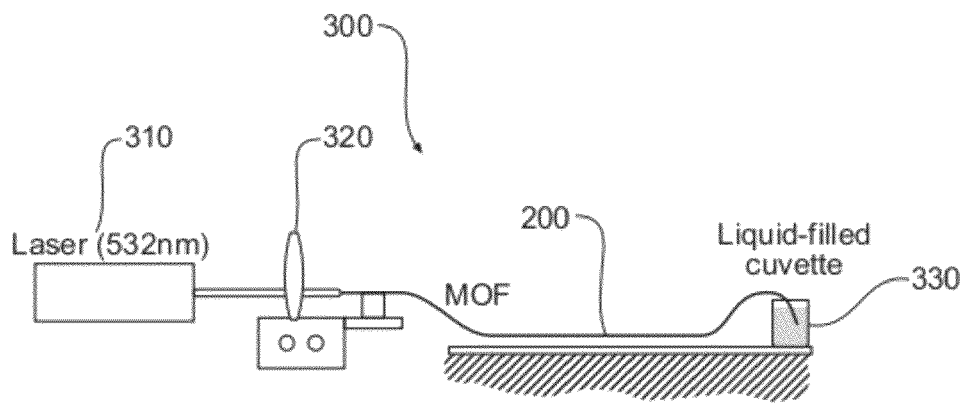
FIG. 3 is a figurative view of a filling length detector for measuring the amount of fluorescent material provided to the sensor shown in FIG. 2.

Referring now to FIG. 3, each of the longitudinal channels 220, 221, 222 is filled with a fluorescent material in liquid form which in this illustrative embodiment is Rhodamine B dissolved in isopropanol. As such, channels 220, 221, 222 form a containment region for containing the fluorescent material in liquid form. The absorption and low concentration fluorescent peaks of Rhodamine B are at 540 nm and 570 nm respectively. Capillary action is used to fill channels 220, 221, 222 from filling container 330 containing the fluorescent material. As can be verified by the filling length detector 300, this capillary action functions to rapidly fill channels 220, 221, 221.

Filling length detector 300 includes a CW laser 310 operating at 532 nm coupled to sensor 200 using an aspheric lens 1220 having a f=2.75 mm and NA=0.65 providing a maximum coupling efficiency of 19%±1%. The position of the fluorescent material in channels 220, 221, 222 is then able to be recorded by observing the fluorescent emission of the liquid interface in the backward direction of the laser beam.

The expected filling rate is calculated based on a filling rate equation for circular capillary tube (see for example Washburn, E. W., *Physical Review,* 17, 273-283 (1921), hereby expressly incorporated by reference in its entirety) where the following values have been assumed for isopropanol.

| Physical Parameter | Value |
| --- | --- |
| Density | 785 kgm$^{-3}$ |
| Surface Tension | 0.022 Nm$^{-1}$ |
| Viscosity | 2.27 × 10$^{-3}$ Nsm$^{-2}$ |
| Effective Radius ($r_{eff}$) | 6.11 × 10$^{-6}$ m |
| Contact Angle | 0 |
| Coefficient of Slip | 0 |
| External Pressure | 0 |

To determine the effective radius $r_{eff}$ of sensor 200, it is assumed that the channels 220, 221, 222 (as best seen in FIG. 2) are circular with the same area as that of sensor 200 as determined by SEM.

Figure 4:
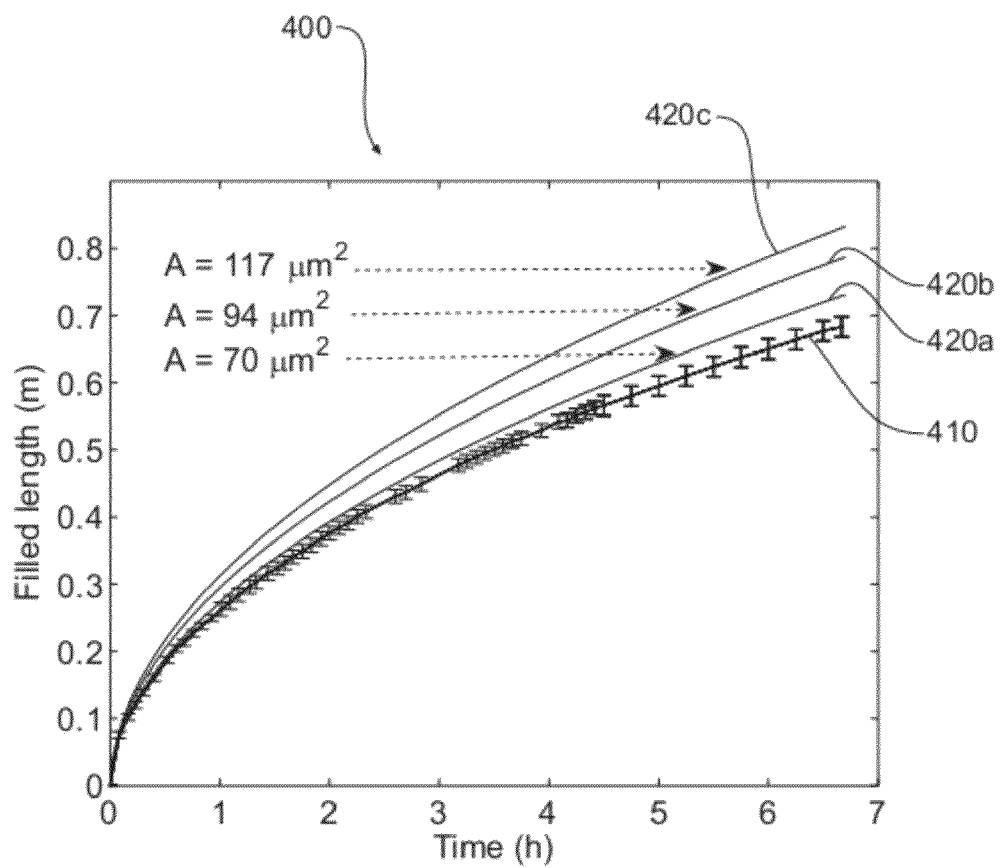
FIG. 4 is a graph comparing theoretical predictions of the filling rate of the sensor shown in FIG. 2 with the measured rate as determined by the filling length detector shown in FIG. 3.

Referring now to FIG. 4, there is shown a graph 400 of the experimental measurements 410 of the filled length as a function of time and the theoretical filling predictions 420a (corresponding to $r_{eff}$=4.72 μm), 420b (corresponding to $r_{eff}$=5.47 μm) and 420c (corresponding to $r_{eff}$=6.11 μm). Although the theoretical result 420c which corresponds to the actual measured $r_{eff}$ overestimates the filled length, it is clear that there is overall agreement between the theoretical prediction and the experimental results.

The small discrepancy between the theoretical prediction and the experimentally determined results is due largely to the assumption that channels 220, 221, 222 are circular. As the action of capillary forces are largely due to surface effects, the assumption of a uniform radius of curvature does not take into account the corner regions of channels 220, 221, 222. This results in an overestimation of the filling rate.

Figure 5:
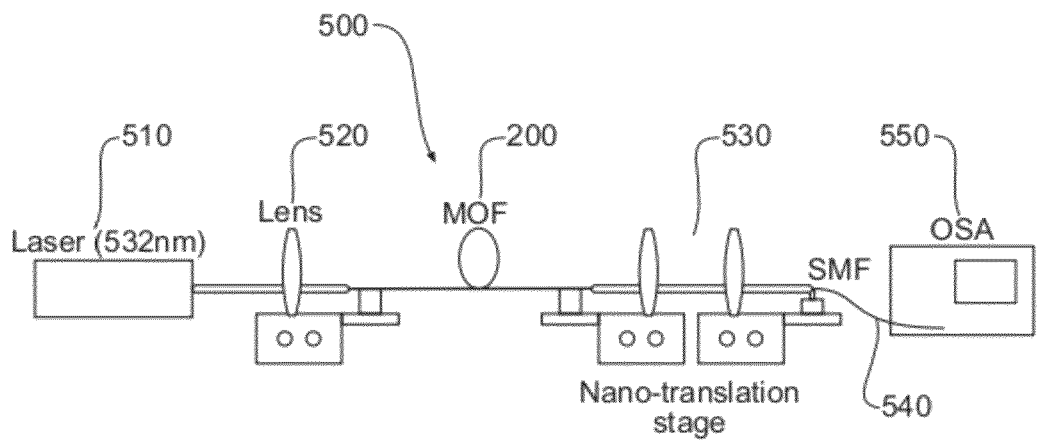
FIG. 5 is a figurative view of a sensor setup for measurement of a fluorescent signal based on the sensor illustrated in FIG. 2.

Referring now to FIG. 5, there is shown sensor setup 500 incorporating sensor 200 which is coupled to a CW laser 1210 operating at 532 nm using an aspheric lens 520 of f=2.75 mm and NA=0.65 providing a maximum coupling efficiency of 19%±1%. The measured loss of sensor 200 at 532 nm is 5.5±0.5 dB/m. From the output of sensor 200, a long pass filter 530 is employed to exclude the excitation frequency components and couple the output light to a single mode fiber (SMF) 540 which is then connected to an optical spectrum analyser (OSA) 550 for spectrum measurement of the fluorescent emission.

In this illustrative embodiment, channels 220, 221, 222 of sensor 200 are coated with a suitable index matching liquid to strip any fluorescent emission coupled to the cladding modes, thereby ensuring that the measured fluorescence from sensor 200 has been captured by the relatively low-loss core-guided modes of the sensor.

Figure 6:
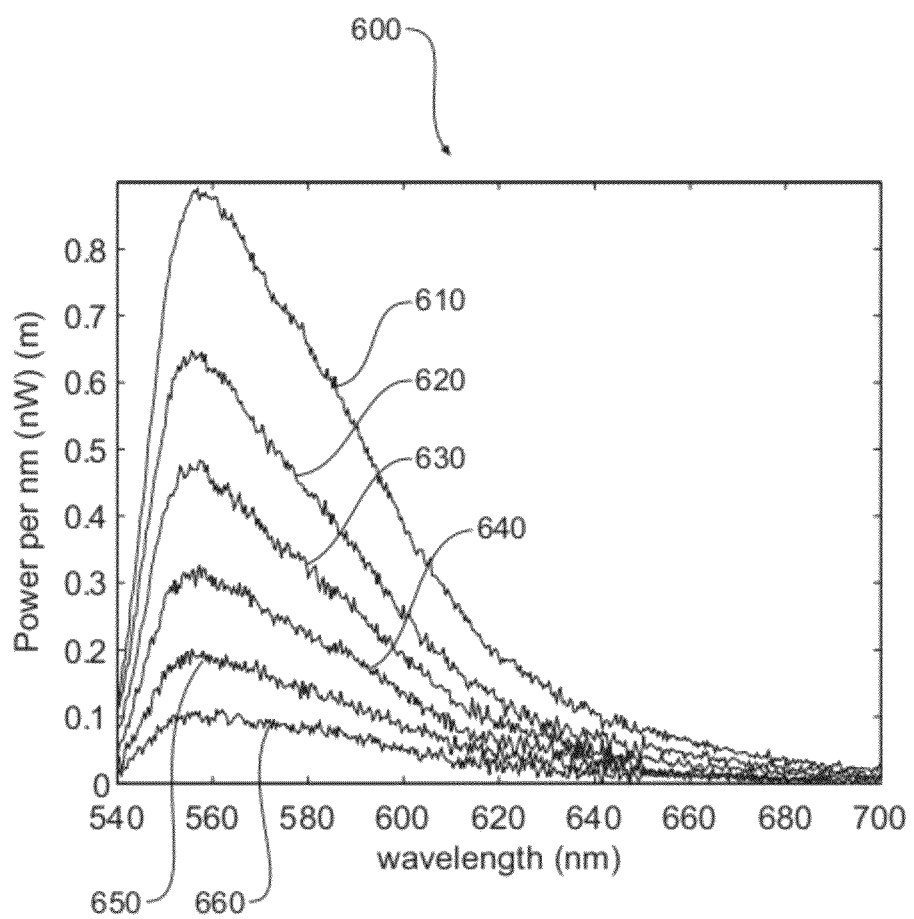
FIG. 6 is a graph of the fluorescent signal detected by the sensor setup illustrated in FIG. 5.

Referring now to FIG. 6, there is shown a graph 600 of the performance of sensor 200 clearly showing the expected fluorescence 620 and also significant decay of the measured fluorescence over time. For example, the fluorescent signal at 72 seconds is shown at 630, the signal at 240 seconds is shown at 640, the signal at 480 seconds is shown at 650 and the signal at 960 seconds is shown at 660. As would be appreciated by those skilled in the art, this decay in fluorescence is due to photobleaching i.e. from the photo-induced destruction of the fluorophore (see for example Rost, F. W. D., *Fluorescent Microscopy,* Cambridge University Press, Cambridge, UK, (1992), hereby expressly incorporated by reference in its entirety).

As has been demonstrated by the applicant here, the configuration of sensor 200 functions to increase the intensity of the light propagating along elongate core portion 210 in an interface region 230, 231, 232 located between the elongate core portion 210 and the interaction region which in this illustrative embodiment comprise the elongate channels 220, 221, 222 that includes the fluorescent material. This enhancement in the intensity at this interface region has the significant advantage of increasing the amount of captured fluorescent light in the elongate core portion 210 resulting from the fluorescence in the interaction region that in this embodiment surrounds the elongate core portion 210.

As will be described in detail later in relation to a method developed by the applicant for simulating the excitation of a fluorescent material to produce fluorescent light and the subsequent recapture and propagation of a proportion of fluorescent light by an elongate core portion in a sensor, the localized high intensity interface regions are formed due to the discontinuity of the electric field at the interface of two dielectric media in this case the Rhodamine B dissolved in isopropanol in the interaction region (or elongate channels 220, 221, 222) and the elongate core portion 210 which is formed of SF57.

The magnitude of this discontinuity is proportional to the ratio of the dielectric constants of the two media and the absolute value of the intensity depends on the diameter of the elongate core 210 and the wavelength of the light. As a result of the overlapping of these localized high intensity regions in the modal field with the fluorescent material, the performance of sensor 200 is substantially enhanced when compared to other solid core MOF based sensors. As would be appreciated by those skilled in the art, sensor 200 thus demonstrates both in-fiber excitation and fluorescent recapturing within a liquid-filled solid core index-guiding MOF through its guided modes.

The use of solid-core fibers in this illustrative embodiment thus allows access to high light-matter overlaps without necessitating selective hole filling as sensor 200 may be passively filled (as illustrated in FIGS. 3 and 4).

Whilst in this illustrative embodiment an organic liquid dye such as Rhodamine B dissolved in isopropanol has been employed, equally any other suitable fluorescent material may be used. One example is the use of quantum dots which are nanometer scale clusters of semiconductor atoms with broad excitation spectrum and narrow, wavelength-tunable fluorescence emission. As would be appreciated by those skilled in the art, quantum dots have a number of advantages over many other fluorescent materials in that they have much higher brightness and photostability resulting in negligible photobleaching.

In another illustrative embodiment employing the use of quantum dots, a quantum dot dye Qdot® 800 that is commercially available from Invitrogen Corporation was employed as the fluorescent material. Qdot® 800 is formed from a CdTe—ZnS quantum dot compound and in this illustrative embodiment is employed to label a biological material comprising goat F(ab')2 anti-mouse IgG conjugate in aqueous solution. Qdot® 800 posseses a broad absorption spectrum that ranges from the UV to near infrared and as suggested by its name the maximum emission wavelength of this material is 800 nm.

The combined quantum dot labeled biological material is then used to fill channels 220, 221, 222 of sensor 200 by capillary action and a sensor setup similar to that shown in FIG. 5 is used with a 532 nm irradiation source with the resulting captured fluorescence detected by an OSA as discussed previously (see for example Ruan, Y., Schartner, E. P., Ebendorf-Heidepriem, H., Hoffman, P., Monro, T. M., "Detection of quantum-dot labeled proteins using soft glass microstructured optical fibers", *Optics Express*, 15, 17819-17826 (2007), hereby expressly incorporated by reference in its entirety).

The applicant here found that concentrations of the biological material as low as 1 nM were detectable via direct measurement of captured fluorescence at the end of sensor 200 for a non-optimized configuration of sensor 200 formed of a commercial lead silicate glass such as SF57, F2 or LLF1 (available from the Schott Glass Company) and having in these illustrative embodiments core diameters of 1.3 μm and 1.9 μm respectively with corresponding strut lengths of 6 μm and 7 μm. Further improvements in performance of these types of biological sensors are expected by further reducing these core sizes and increasing strut lengths of sensor 200.

Additionally, the fluorescent material may include materials that are directly coated or functionalized onto or near the interface regions. In one illustrative embodiment, the fluorescent material is a fluorescently labeled antibody for the detection of a predetermined bio-molecule. In this embodiment, interface regions 230, 231, 232 may be coated with one or more different fluorescently labeled antibodies.

In accordance with this embodiment, a sensor 200 formed of F2 soft glass and having a 1.3 μm core diameter was employed. The channels 220, 221, 222 were first silanized by pumping 3-Mercaptopropyltrimethoxysilane [Sigma] into each channel followed by N-γ-maleimidobutyryloxy succinimide ester (GMBS) [Merck] which forms a cross linking layer on the silanized internal surfaces of channels 220, 221, 222. The cross linking layer functions to connect the silane layer to the antibody which in this example was 100 nM Qdot® 800 goat F(ab')2 anti-mouse IgG conjugate which is subsequently pumped through channels 220, 221, 222. Between the respective attachment of the silane, crosslinker and antibody layers the channels were washed with an aqueous buffer solution.

Once again sensor 200 was deployed in a sensor setup similar to that shown in FIG. 5 and irradiated using a 532 nm irradiation source. Fluorescence was detected (see for example, Monro, T. M., Ruan, Y., Ebendorf-Heidepriem, H., Foo, H., Hoffman, P., Moore, R. C., "Antibody immobilization within glass microstructured fibers: a route to sensitive and selective biosensors", 19th International Conference on Optical Fibre Sensors, Perth, Australia, Apr. 14-18, 2008, *Proceedings of SPIE*, 7004, (Post Deadline Paper) (2008), hereby expressly incorporated by reference in its entirety) thereby demonstrating that the antibodies had been immobilized on the internal surfaces of channels. Accordingly, sensor 200 incorporating the immobilized antibodies in channels 220, 221, 222 may then be flushed through with biological material containing the bio-molecules (i.e. the specific antigen) that are being sought to be detected via bonding to immobilized antibodies.

The presence and concentration of these bio-molecules can then be determined by activating sensor 200 by propagating light of a suitable excitation wavelength down core 210. In another illustrative embodiment, biological fluids may be allowed to continuously flow through channels 220, 221, 222 with sensor 200 left permanently in the "on" state.

In those instances where the fluorescent material is directly coated onto the interface region as a thin layer it has been found that any resulting fluorescence is more likely to be captured. (see for example Warren-Smith, S. C., Afshar, V. S., Monro, T. M., "Highly-efficient fluorescence sensing using microstructured optical fibers; side-access and thin-layer configurations", 19th International Conference on Optical Fibre Sensors, Perth, Australia, Apr. 14-18, 2008 *Proceedings of SPIE*, 7004, 99 (2008), hereby expressly incorporated by reference in its entirety.) However, the absorption of this thin layer still needs to be greater than any corresponding fiber losses to provide an enhancement of the resultant fluorescence signal. These thin layer fluorescent material configurations can increase the fluorescence capture efficiency by approximately 250% when compared to equivalent sensor configuration where the fluorescent material completely fills the channels as has been described previously.

To facilitate the development of other sensor geometries a method of simulating the excitation of a fluorescent material to produce fluorescent light and the subsequent recapture and propagation of a proportion of fluorescent light by an elongate core portion in a sensor in accordance with the present invention is described. This method takes into account the significant excitation-fluorescence wavelength separation such as would be expected with quantum dots, the presence of wavelength-scale features in MOFs and high contrast refractive indices.

The method makes use of vectorial solutions to Maxwell's equations and includes the fiber losses at both excitation and fluorescence wavelengths. This formalism can be applied to arbitrary fiber cross-sections. By evaluating the modal characteristics of a range of fibers at both wavelengths, ways of enhancing the sensing sensitivity by maximising the fluorescent capture fraction (FCF) within the guided mode(s) of the fiber may be explored.

Referring once again to FIG. 1, which depicts the general geometry for a MOF based sensor, the simulation method assumes that the propagating modes of an absorbing MOF are the same as nonabsorbing ones except that their powers decay with an attenuation factor of γ as they propagate. The excitation electromagnetic power in the j th mode at excitation frequency $\omega_E$ is then expressed as $$P_{Ej}(z) = |a_{Ej}|^2 N_{Ej} \exp(-\gamma_{Ej} z); \ N_{Ej} = \frac{1}{2} \text{Re} \left\{ \int_{A_\infty} (e_{Ej} \times h^*_{Ej}) \cdot \hat{z} dA \right\} \quad (1)$$

$$\gamma_{Ej} = k \left( \frac{\varepsilon_0}{\mu_0} \right)^{1/2} \frac{\int_{A_\infty} n_E n^i_E |e_{Ej}|^2 dA}{N_{Ej}}. \quad (2)$$

(see for example Snyder, A. W. and Love, J. D., *Optical Waveguide Theory*, Chapman and Hall, 2-6 Boundary Row, London SE1 8HN, UK, (1995), hereby expressly incorporated by reference in its entirety) where $\alpha_{Ej}$ is the expansion coefficient for mode j, $e_{Ej}(x,y)$, $h_{Ej}(x,y)$, $\beta_{Ej}$, and $\gamma_{Ej}$ are the j th mode electric and magnetic field distributions, propagation constant and power decaying factor due to absorption, respectively. Here, it is assumed that $\gamma_j$ is representing all absorption mechanisms in the MOF, including absorption due to the Beer-Lambert law (see for example Rost, F. W. D., *Fluorescent Microscopy*, Cambridge University Press, Cambridge, UK, (1992), referred to earlier).

For an arbitrary filled MOF, both $n_E(x, y)$ and $n_E^i(x,y)$ (real and imaginary parts of refractive indices) are functions of transverse coordinates and hence the piece-wise integral in Equation (2) can be integrated over the glass and channels which define the interaction regions. Equation (1) indicates that although the absorption of the excitation mode occurs in the filled region, through the Beer-Lambert law, the peak intensity also reduces, keeping the shape of the mode and the hole power fraction constant.

Upon absorbing the excitation photons, the fluorescent material in the channels behave as new sources and emit fluorescent photons in all directions. Similar to the excitation field, the emission of this new fluorescent source can in general be written as the sum of forward, backward, and radiation modes of the non-absorbing MOF with the consideration of power decay due to loss at the fluorescent frequency. Accordingly, it is found that the fluorescent power propagating through the j th forward mode of the MOF, including its loss, is $$P_{Fj}(z) = \frac{\pi^2 \exp(-\gamma_{Fj} z)}{\omega_F \mu_0 n_F^H k N_{Fj}} \int_V |e_{Fj}|^2 P_D(r) \exp(\gamma_{Fj} z) dV. \quad (3)$$

(see for example Marcuse, D., *Journal of Lightwave Technology*, 6, 1273-1279 (1988), hereby expressly incorporated by reference in its entirety).

Figure 1:
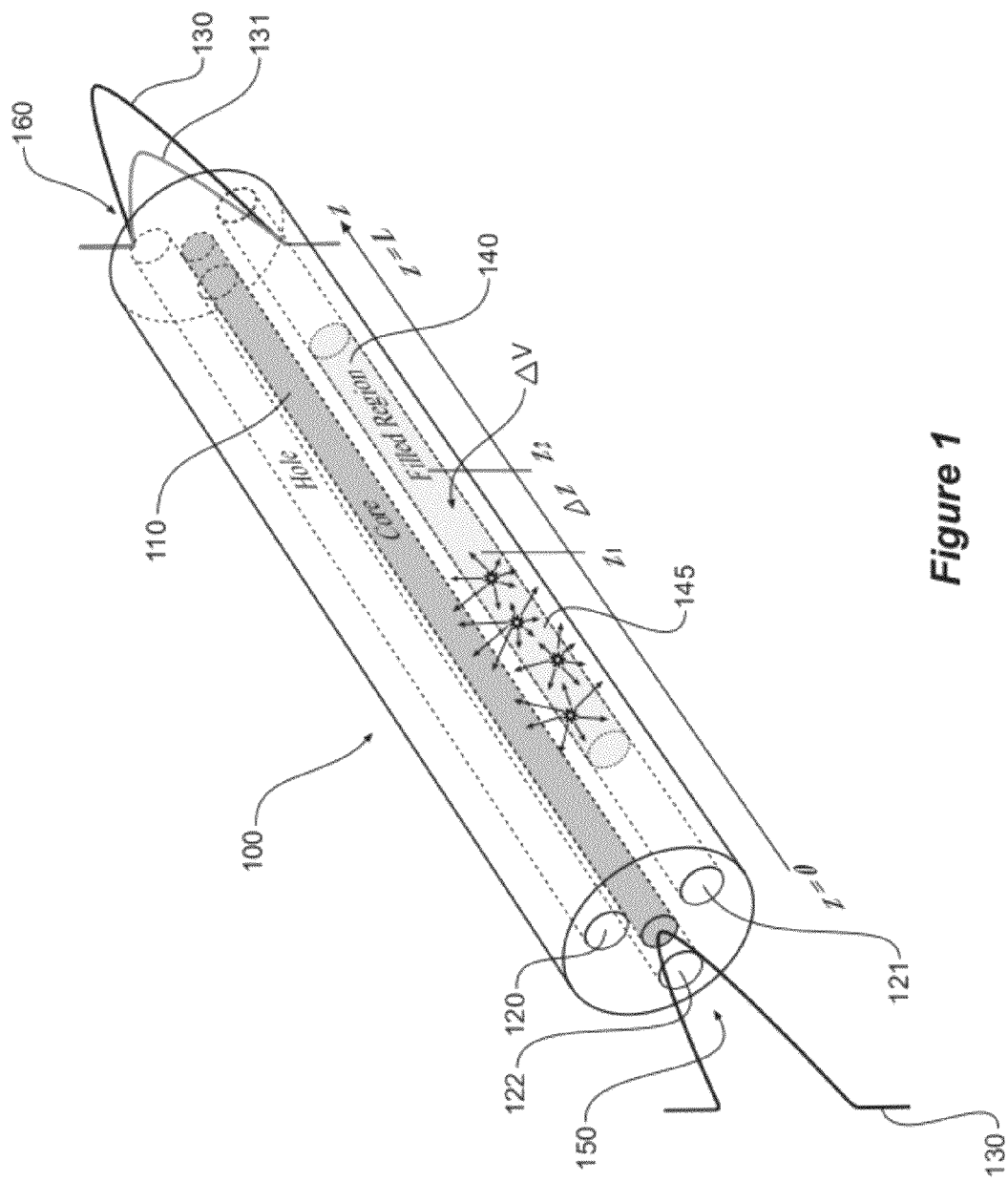
FIG. 1 is a figurative side perspective view of a MOF sensor configuration based on fluorescence spectroscopy.

Here, $P_D(r)$ is the radiation power density of any sources within the MOF, which for the case considered here is due to the fluorescent emission of the filling material. The density of fluorescent emission at point r depends on the absorption of excitation field from the beginning of the filled area up to the point r, (as best seen in FIG. 1). Using Equations (1) and (2) and assuming that the efficiency of excitation absorption to fluorescent emission is $\xi$, it is found that $P_D(r)$ as $$P_D(r) = \quad (4)$$
$$\xi \lim_{\Delta V \to 0} \frac{absorbed power}{\Delta V} = \frac{1}{2} \xi \alpha_B \eta^H_{Ej} |a_{Ej}|^2 \text{Re}[(e_{Ej} \times h^*_{Ej}) \cdot \hat{z}] \exp(-\gamma_{Ej} z).$$

Here $\eta_{Ej}^H = n_E^H (\varepsilon_0/\mu_0)^{1/2} 1/(2N_{Ej}) \int_H |e_{Ej}|^2 dA$ is a generalization of the usual definition of power fraction, i.e., $\int_H (e_x^2 + e_y^2) dA / \int_{A_\infty} (e_x^2 + e_y^2) dA$, $\alpha_B = \in_\lambda C$ is the absorption coefficient due to Beer-Lambert law, where $\in$ is the molar extinction coefficient of the filling material and C is the molar concentration, and superscript H refers to the channel regions.

Substituting Equation (4) into Equation (3), and taking the integral over z, the fluorescent capture fraction FCF into the j th guided mode of the MOF can be expressed as $$FCF = P_{Fj}(z)/P_{Ej}(0) = AB \frac{\exp(-\gamma_{Fj} z)}{(\gamma_{Ej} - \gamma_{Fj})} \{1 - \exp[(\gamma_{Fj} - \gamma_{Ej})L]\}; \ z > L \quad (5)$$

$$A = \frac{\xi \alpha_B \lambda^2}{2n_F^H}; \ B_j = n_F^H \left( \frac{\varepsilon_0}{\mu_0} \right)^{1/2} \frac{\eta_{Ej}^H \int_H |e_{Fj}|^2 \text{Re}[(e_{Ej} \times h^*_{Ej}) \cdot \hat{z}] dA}{4 N_{Fj} N_{Ej}}. \quad (6)$$

In this equation A is a constant coefficient, $P_{Ej}(0)$ is the input excitation field power at the beginning of the filled part of the fiber, whose length is shown by L (see FIG. 1). Throughout the description only the FCF into the fundamental guided mode is considered.

Figure 7:
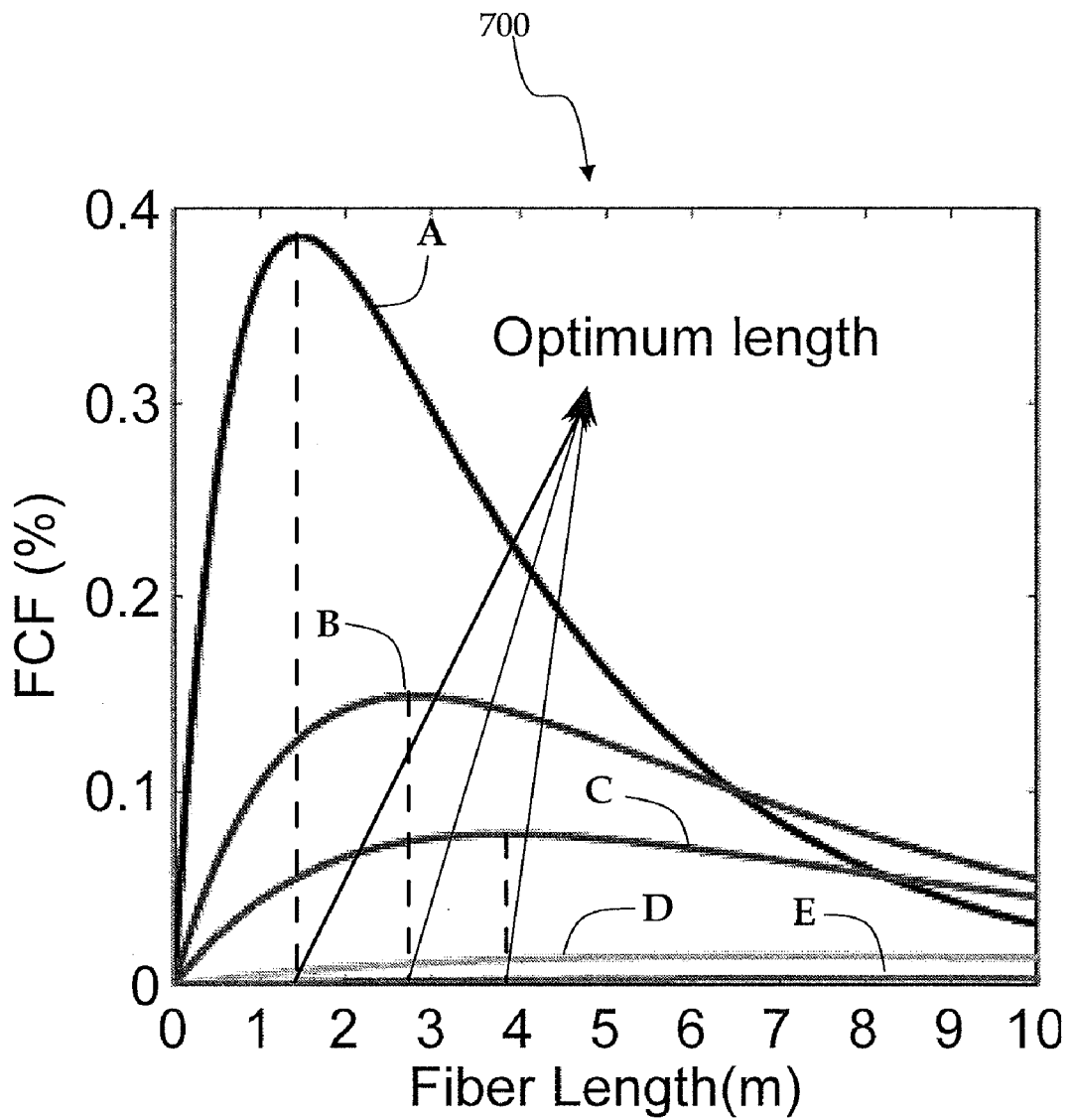
FIG. 7 is a graph of the calculated fluorescent capture function (FCF) as a function of fiber length for the sensor geometry shown in FIG. 2 for an assumed core diameter of 0.8 μm, at a wavelength of 590 nm and assuming a $5\times10^{-5}$ M concentration of Rhodamine B dissolved in isopropanol (refractive index of 1.3774) for a range of materials of varying refractive index.

Referring now to FIG. 7, there is shown a graph 700 of the results of calculating the FCF as a function of fiber length for the geometrical configuration of sensor 200 (as best seen in FIG. 2). The core diameter, d, is defined to be the diameter of a circle 260 with area equal to that of the largest equilateral triangle that fits wholly within the substrate core region. An idealized MOF structure is defined where the curvature of the core is approximated by the edges of the three dashed circles 270 connected by the bases of three rectangles approximating the struts. To solve Maxwell's equations for this geometry, a commercial FEM package COMSOL 3.2 is used.

Graph 700 clearly shows that there is an optimum fiber length $L_{opt} = \ln(\gamma_F/\gamma_E)/(\gamma_F - \gamma_E)$, which leads to maximal FCF for any fiber geometry. FCF is shown as a function of fiber length for different substrate glasses as indicated in the table below and for a core diameter of d=0.8 μm.

| Reference | Material | Refractive Index (n) |
| --- | --- | --- |
| A | Silica | 1.45838 |
| B | LLF1 | 1.54799 |
| C | F2 | 1.61983 |
| D | SF57 | 1.84625 |
| E | Bi | 2.08951 |

As would be apparent to those skilled in the art, the above table is not exhaustive as the present invention can be applied to a large range of materials of suitable refractive index including polymer materials and soft glasses including but not limited to lead silicates, bismuthates, tellurites and chalcogenides.

For $L < L_{opt}$ increasing the fiber length increases the absorption in the filled region via the Beer-Lambert law, and thus increases FCF. Beyond this optimum length, however, fiber attenuation dominates and hence the fluorescent power decays as $\exp(-\gamma_{Fj} L)$. As would be generally expected, the use of lower index glasses results in a higher FCF since the relatively low core-cladding index contrast leads to a higher light-matter overlap within the channels (this is also evident in the behaviour of $A_{eff}$ behavior in FIG. 9).

Figure 8:
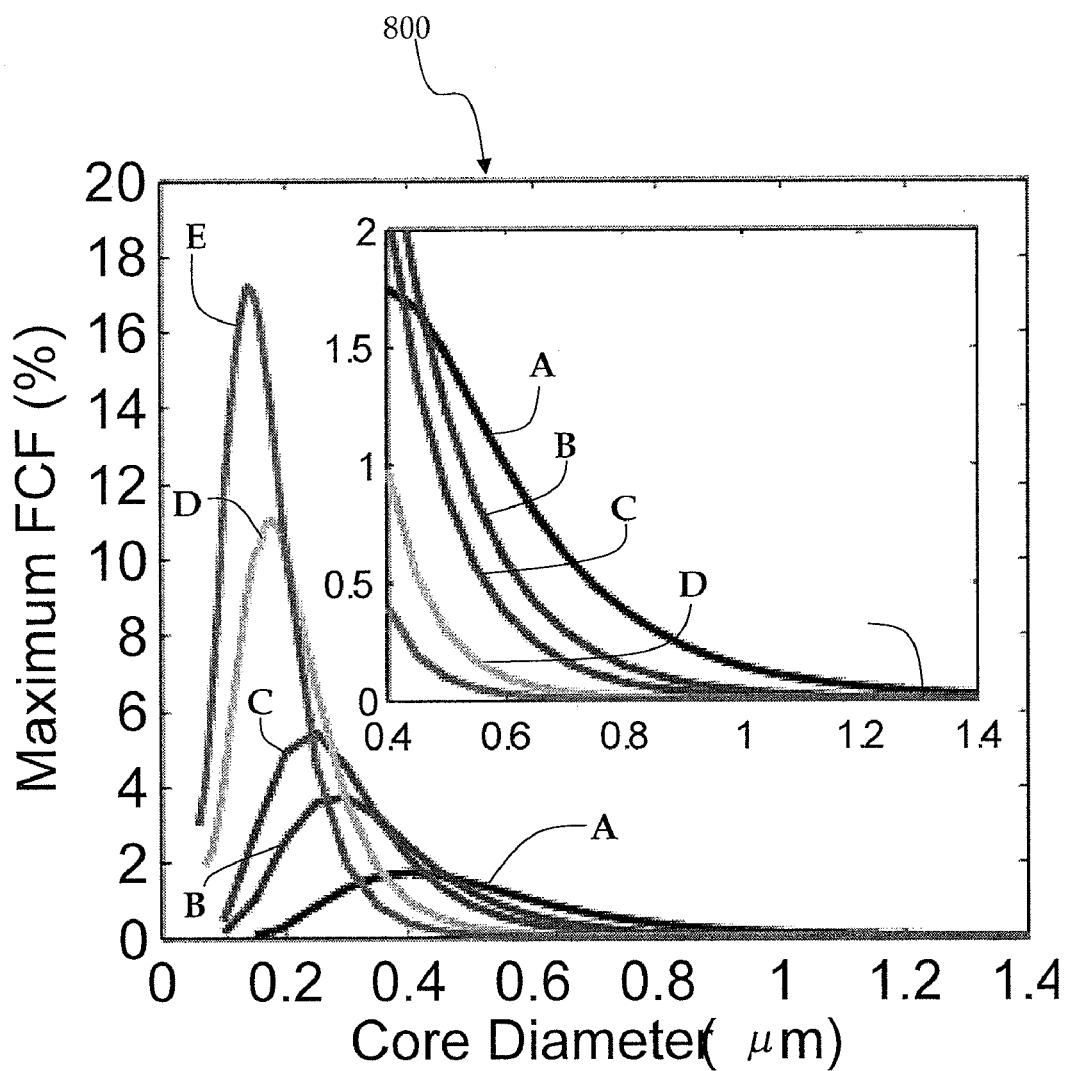
FIG. 8 is a graph of the calculated fluorescent capture function (FCF) as a function of core diameter for the sensor geometry shown in FIG. 2, at a wavelength of 590 nm and assuming a $5\times10^{-5}$ M concentration of Rhodamine B dissolved in isopropanol (refractive index of 1.3774) for a range of materials of varying refractive index, the inset graph depicts a magnified portion for core diameters greater than 0.4 μm.

Referring now to FIG. 8, there is shown a graph 800 of the results of calculating the FCF as a function of core diameter and material type. For small core diameters (d<0.4 μm), the FCF can be significantly enhanced by moving to high index (soft) glasses. FIG. 8 shows the maximum FCF which occurs at fiber length $L_{opt}$, as a function of core diameter. For example, the maximum FCF for a bismuth-oxide fiber, which occurs for a core size of d=0.2 µm, is 18%, 9 times larger than the maximum FCF value for silica fibers (2%), which occurs for a core size of d≈0.4 µm, and 27 times larger than the FCF of silica for d~0.2 µm To understand this effect, it is useful to examine coefficient $B_j$ in Equation (6) which depends on the field distributions of the guided modes of the fiber and their overlap with the materials within the channels. It is assumed that the mode profiles of the excited and fluorescent fields are the same (i.e., $N_{Fj}=N_{Ej}$), which although not strictly true especially for filling materials such as quantum dots with large separation of absorbing and fluorescent wavelengths, can help provide physical insight. The coefficient $B_j$ can then be rewritten as $B_j=NOI_j/A_{eff}$ where;

$$NOI_j = n_F^H \left(\frac{\varepsilon_0}{\mu_0}\right)^{1/2} \frac{\eta_{Ej}^H \int_H |e_j|^2 \text{Re}[(e_j \times h_j^*).\hat{z}]dA}{\int_{A_\infty} |\text{Re}[(e_j \times h_j^*).\hat{z}]|^2 dA}; \quad (7)$$

$$A_{eff} = \frac{\left(\int_{A_\infty} \text{Re}[(e_j \times h_j^*).\hat{z}]dA\right)^2}{\int_{A_\infty} |\text{Re}[(e_j \times h_j^*).\hat{z}]|^2 dA}.$$

Here $NOI_j$ is a normalized field-matter overlap integral, which approaches 1 when the core diameter becomes very small (see FIG. 10), reflecting the fact in the limit of vanishing core size, all of the light is located outside the core. $A_{eff}$, defined based on z component of the Poynting vector, is a generalized form of the usual definition of $A_{eff}$ (see for example Agrawal, P., *Nonlinear Fiber Optics*, Academic Press, (2007), hereby expressly incorporated by reference in its entirety).

Figure 9:
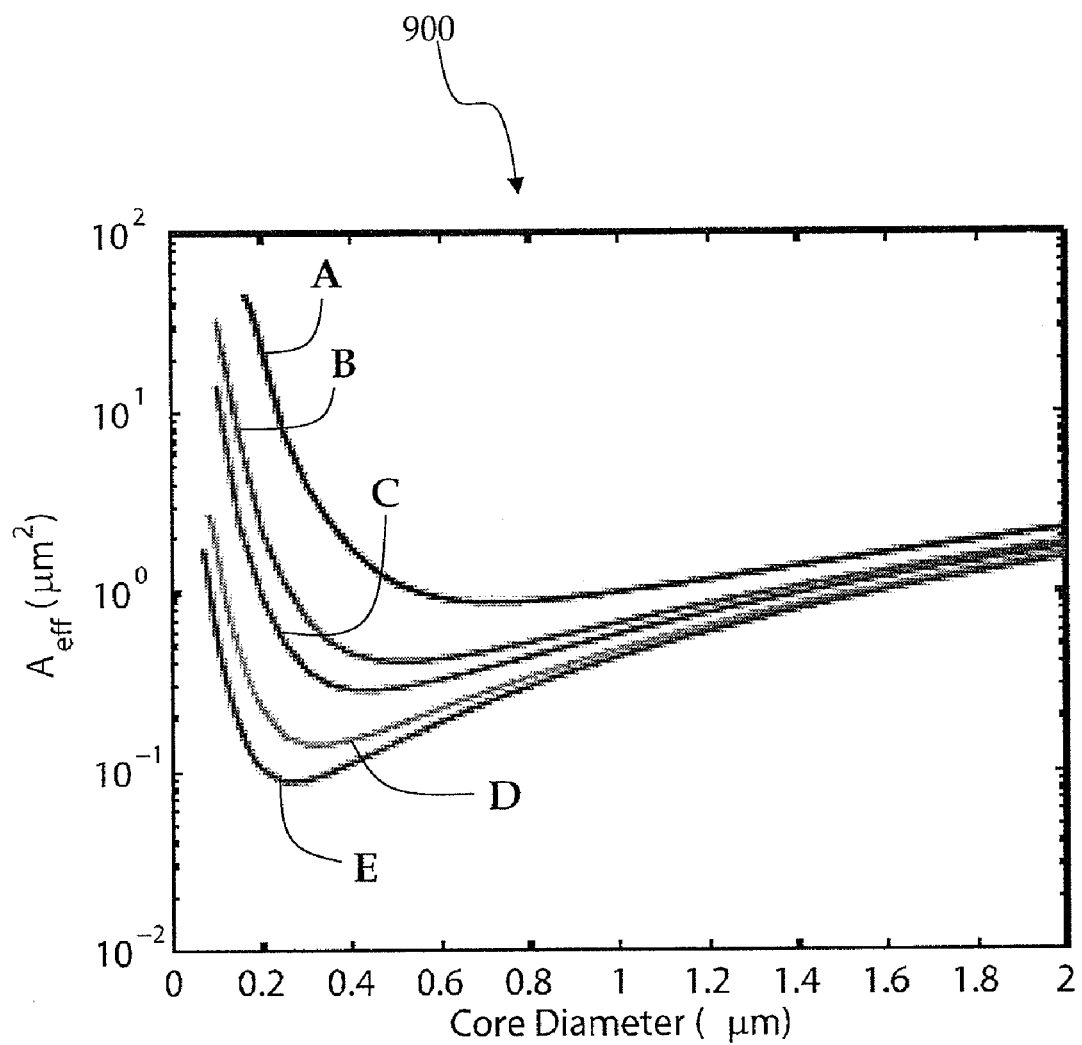
FIG. 9 is a graph of the calculated effective area $A_{eff}$ of the fundamental mode as a function of core diameter for the sensor geometry shown in FIG. 2, at a wavelength of 590 nm and assuming a $5\times10^{-5}$ M concentration of Rhodamine B dissolved in isopropanol (refractive index of 1.3774) for a range of materials of varying refractive index.
Figure 10:
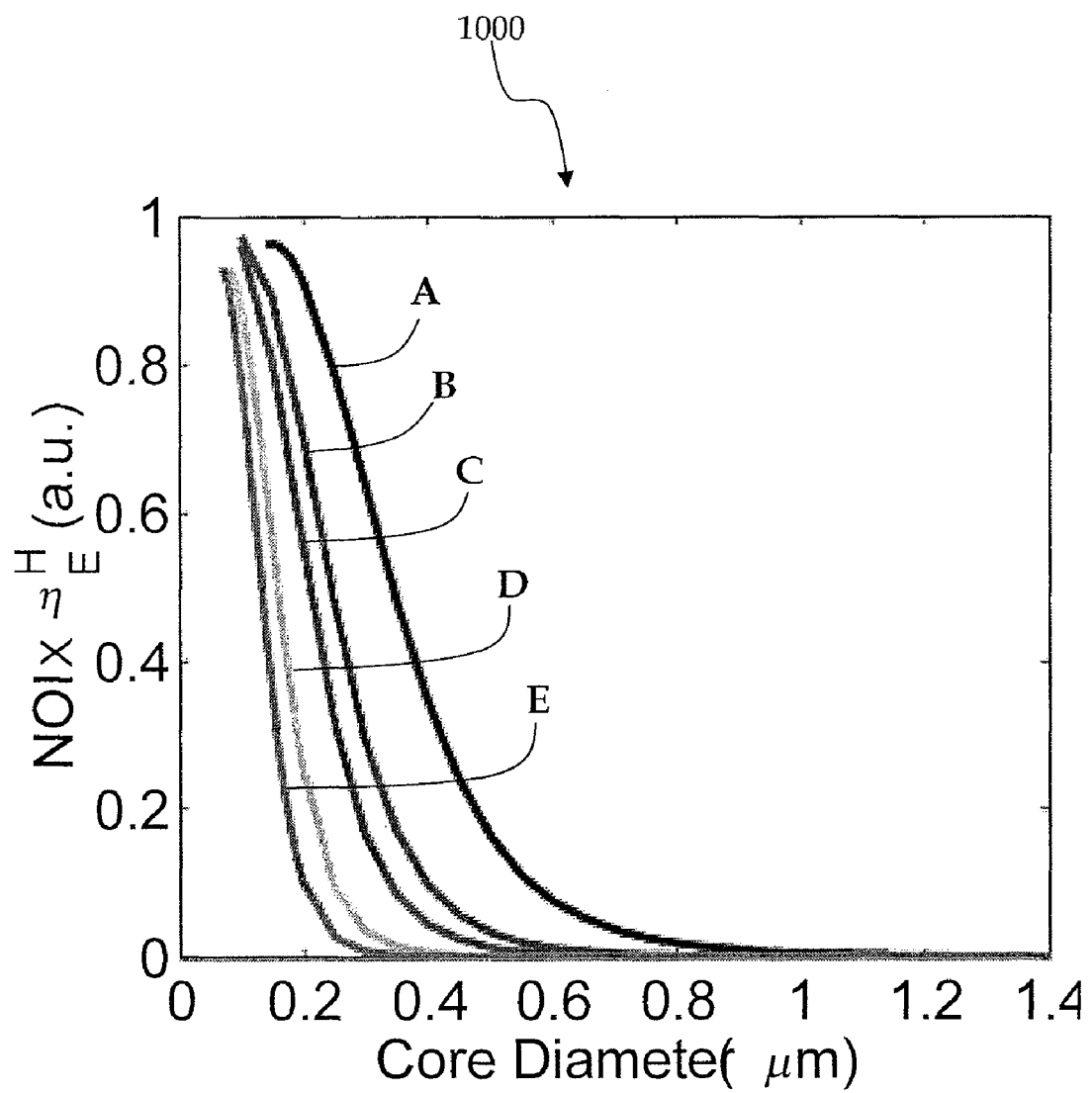
FIG. 10 is a graph of the calculated normalized overlap integral (NOI) as a function of core diameter for the sensor geometry shown in FIG. 2, at a wavelength of 590 nm and assuming a $5\times10^{-5}$ M concentration of Rhodamine B dissolved in isopropanol (refractive index of 1.3774) for a range of materials of varying refractive index.

Referring now to FIGS. 9 and 10, inspection of calculated values for $A_{eff}$ 900 and NOI 1000 at d=0.2 µm for silica (i.e. A) and bismuth (i.e. E) reveals that although the NOI for silica is 9 times larger than that of bismuth, indicating a much larger field-channel overlap, the effective area, $A_{eff}$, of the propagating mode for bismuth is 240 times smaller than that of silica for this core diameter, resulting in higher intensity values for bismuth and thus a larger FCF.

Figure 12:
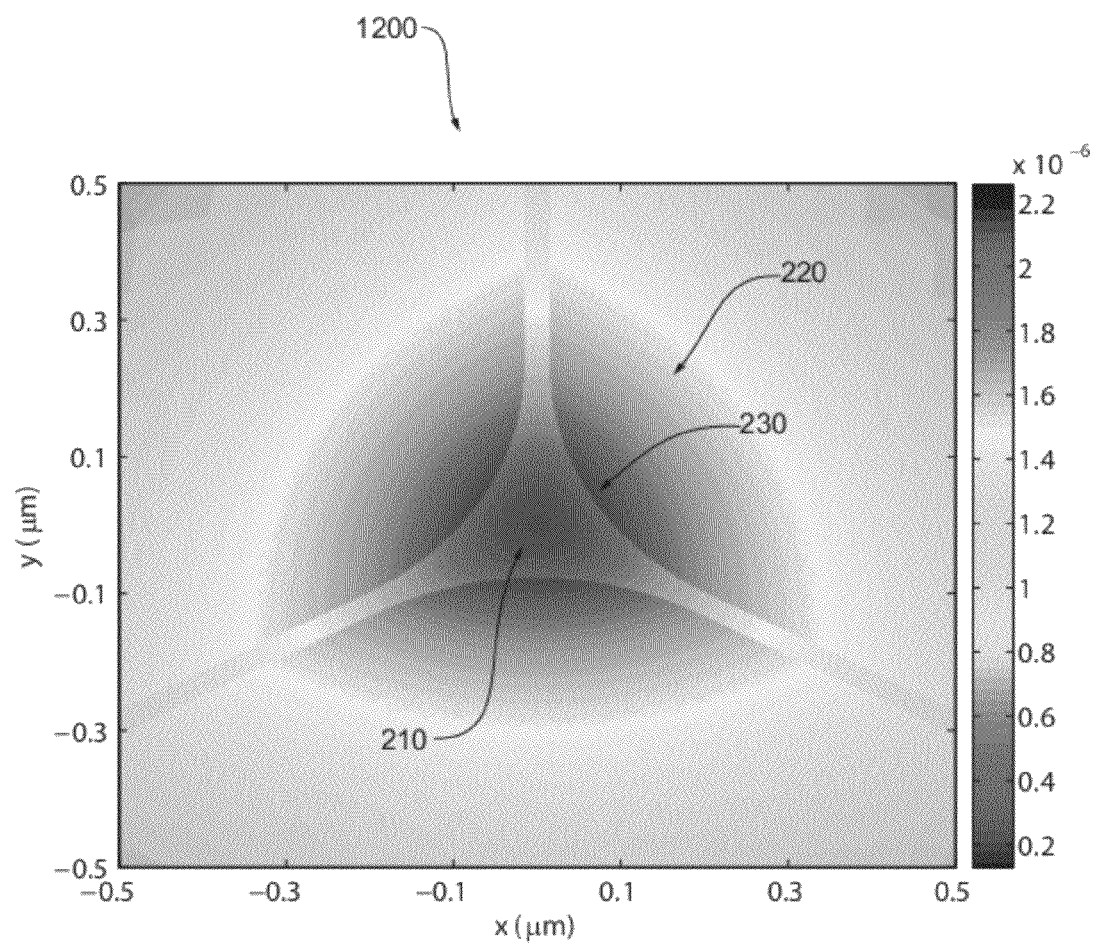
FIG. 12 is a graph of the calculated intensity distribution of the fundamental mode for the sensor geometry shown in FIG. 2 formed of silica and having a core diameter of 0.2 μm at a wavelength of 590 nm.
Figure 13:
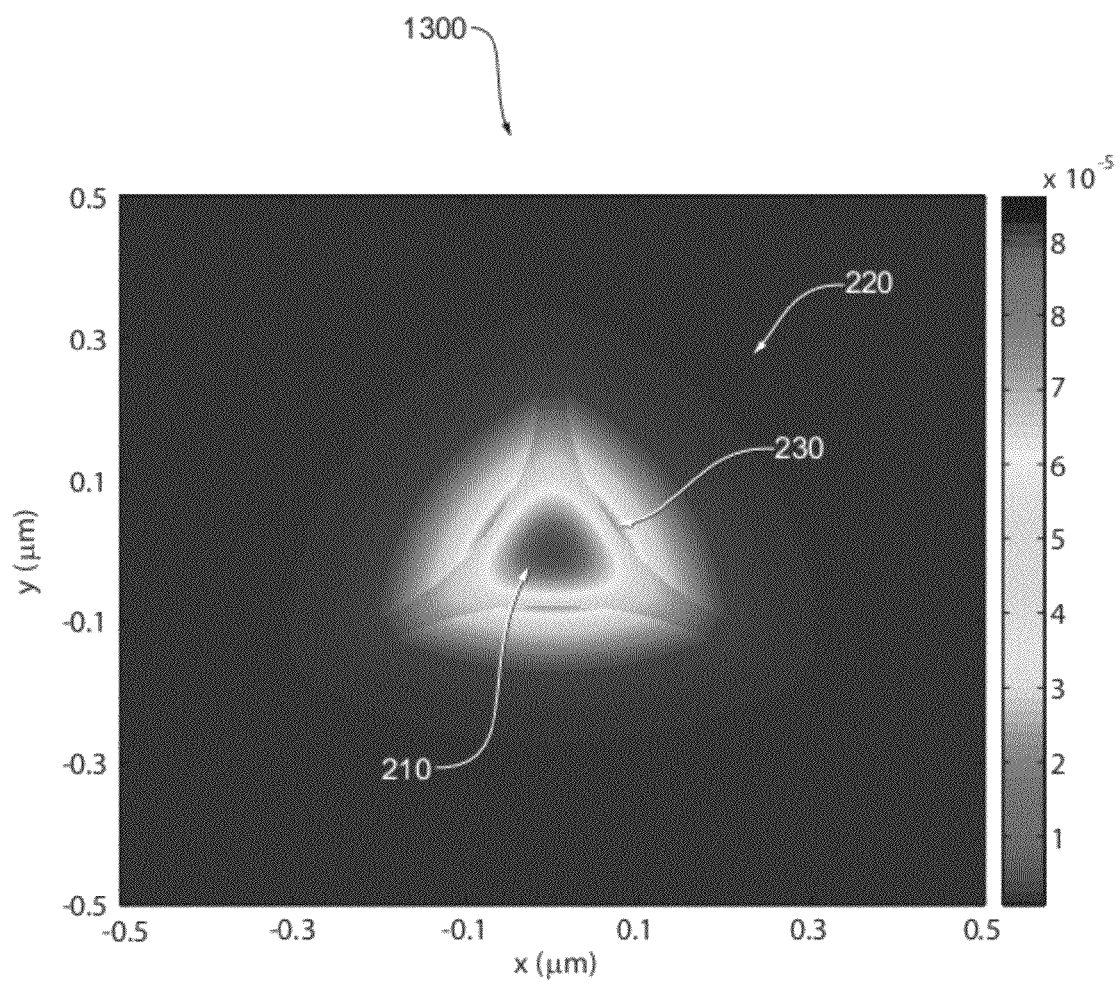
FIG. 13 is a graph of the calculated intensity distribution of the fundamental mode for the sensor geometry shown in FIG. 2 formed of SF57 and having a core diameter of 0.2 μm at a wavelength of 590 nm.

Referring now to FIGS. 12 and 13, there is shown the calculated intensity profiles of the fundamental mode for silica (FIG. 12) 1200 and bismuth (FIG. 13) 1300. Comparison of these figures clearly shows that while the mode is well expanded into the channel or interaction region 220 in the case of silica, it is well confined within the core 210 for bismuth and forms a high intensity thin layer at an interface region 230 located between the core 210 and the interaction region 220.

As has been discussed earlier and simulated in accordance with the method described above, these localized high intensity regions are formed due to the discontinuity of the electric field at the interface of two dielectric media. The magnitude of the discontinuity is proportional to the ratio of the dielectric constants of the two media and hence soft glasses with higher refractive indices result in higher intensities at the interface region located between the interaction region 220 (e.g. channel or hole) and the elongate core 210 (e.g. glass core).

Accordingly, this enhanced FCF regime, achieved by the use of small core dimensions and high index glasses also enhances the sensitivity of FCF to concentration variations. Using Equation (5), the FCF can be approximated to have the form $[1-\exp(-\in_\lambda C \eta_{Ej}^H)]$ as a function of concentration C, which simplifies to a linear form of $\in_\lambda C \eta_{Ej}^H$ in the limit of small concentration.

Figure 11:
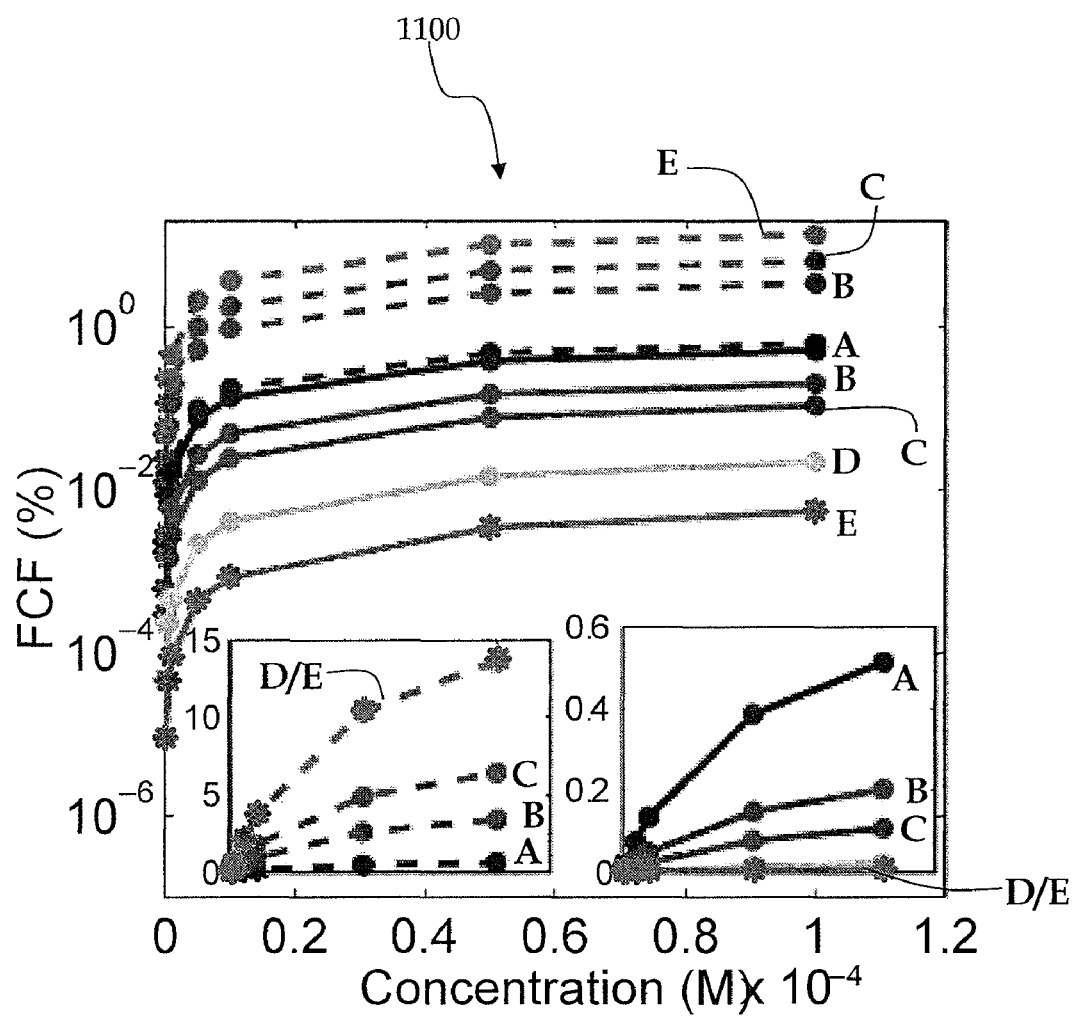
FIG. 11 is a graph of the calculated fluorescent capture function (FCF) as a function of molar concentration of Rhodamine B dissolved in isopropanol (refractive index of 1.3774) for the sensor geometry shown in FIG. 2 for a range of materials of varying refractive index at a wavelength of 590 nm where the dashed lines correspond to a core diameter of 0.2 μm and the solid lines correspond to a core diameter of 0.8 μm, the inset graphs depict a linear scale over the same concentration range.

Referring now to FIG. 11, there is shown a graph 1100 of calculated results of the behaviour of FCF as a function of C for two core diameters d=0.8 (solid lines) and d=0.2 µm (dashed lines) and a range of different glasses. Note however that the behaviour of FCF as a function of C is opposite for small and large core regimes.

FIG. 11 and its insets, reveal that while for large core diameter, e.g., d=0.8 µm silica has the largest asymptotic FCF value and slope, $\partial(FCF)/\partial C$, values of ~0.5% and ~0.0058%/µM, respectively, for small core diameter, e.g. d=0.2 µm bismuth has the largest corresponding values of FCF ~14% and $\partial(FCF)\partial C$ ~0.175%/µM. As a result, both FCF and its sensitivity to small variations in concentration are enhanced in the small core, high index glass regime. Accordingly, this regime is of particular practical benefit for sensors to observe captured fluorescence at extremely low sample concentrations given the substantial fluorescent capturing enhancement of the order of 29 times by using a sensor with high index substrate glasses (e.g. Bi) and small core diameters (e.g. d=0.2 µm) resulting in localized, high intensity regions of light.

As would be apparent to those skilled in the art, the configuration of sensor 200 is only one example of a configuration that may be employed in accordance with the present invention. Some other configurations that are within the scope of the invention include fibers having multiple cores or one or more exposed core regions which may alleviate the requirement to specifically "fill" the interaction regions of a sensor. Another alternative includes sensors having localized access holes to allow filling at selected points along the fiber. Some of these configurations will now be described.

Referring now to FIGS. 14A to 14F, there are shown cross sectional profile views of a variety of sensors 10 in accordance with a number of illustrative embodiments of the present invention. In these various illustrative embodiments the cores may be in the form of nanowires. FIGS. 14A and 14B depict sensors 10 having a single core 16 supported by four radial support struts 14 forming a support structure that extends from an outer or cladding region 12 which in turn forms a supportive outer jacket. This configuration defines four longitudinal channels 18 or interaction regions that can contain fluorescent material. In accordance with the present invention, the size and/or refractive index of the core 16 are adapted to increase the intensity of light propagating or guided by the core 16 at an interface region which throughout these figures has been shaded in grey. FIG. 14B depicts a sensor 10 having non regular shaped struts 14.

FIGS. 14C and 14D depict sensors 10 having a pair of cores 16a, 16b which are supported by struts 14 which in FIG. 14C adopt a first configuration where a central support strut is shared between the two cores 16a, 16b and in FIG. 14D a second configuration where each of the cores 16a, 16b is individually supported. Similarly, FIGS. 14E and 14F depict sensors 10 having three cores 16a, 16b, 16c and four cores 16a, 16b, 16c, 16d respectively. Once again the enhanced interface regions have been shaded in grey. As would be apparent to those skilled in the art, the present invention may be adapted to a large range of geometries depending on the application.

Figure 15A:
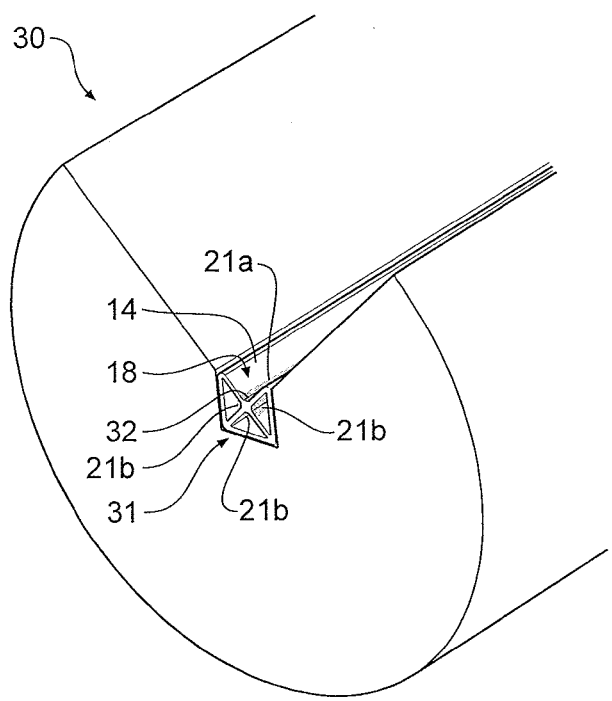
FIGS. 15A and 15B are perspective views of sensor configurations of the exposed core variety in accordance with further embodiments of the present invention.
Figure 15B:
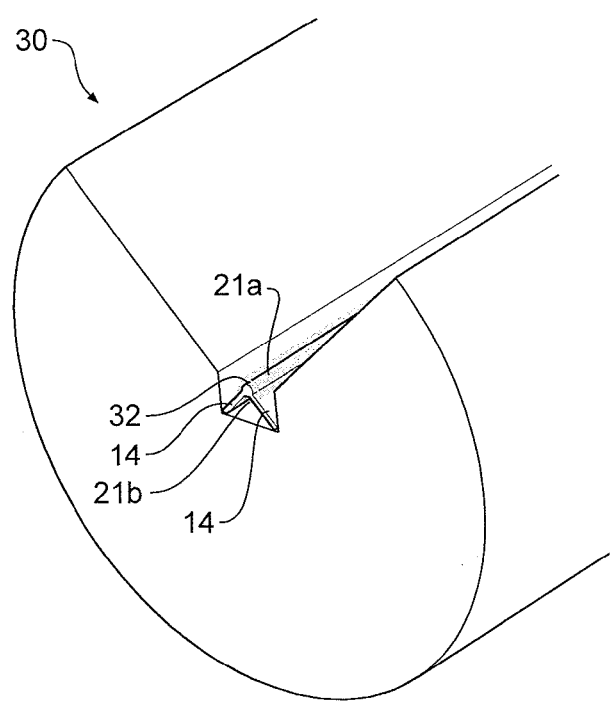

Referring now to FIGS. 15A and 15B, there are shown perspective views of sensors 30 according to further illustrative embodiments of the present invention. In FIG. 15A, a support structure in the form of struts 14 is disposed to provide one "air" channel 18 and three liquid channels and an elongate core 32. In this configuration, one enhanced interface region 21a will be exposed to the environment while three of the enhanced interface regions 21b will not be so exposed but will still be available to receive liquid such as a fluorescent material in solution.

In another alternative embodiment, sensor 30 may be immersed in liquid and hence in this case the three non-exposed channels 21b will correspond to three "air" channels with the liquid being the sensed environment in the exposed channel 21a. This will result in a raised refractive index in the sensing region 21a which has the effect of spreading the mode into the sensing region and for sufficiently small core sizes this will deliver greater optical power in this region.

This then allows sensors of this configuration to perform similarly to a fully filled fiber where each of the channels are filled with the liquid to be sensed (see for example, Warren-Smith, S. C., Afshar, V. S., Monro, T. M., "Theoretical study of liquid-immersed exposed-core microstructured optical fibers for sensing", Optics Express, 16, 12, 9034-9045 (2008), hereby expressly incorporated by reference in its entirety). FIG. 15B illustrates an alternative configuration of sensor 30 where there is a single exposed enhanced interface region 21a and one enclosed or sealed interface region 21b.

As has been discussed in our earlier applications (PCT Publication No. WO2007/041792 entitled "FABRICATION OF NANOWIRES" and PCT Publication No. WO 2007/041791 entitled "METHOD AND DEVICE FOR FORMING MICROSTRUCTURED FIBRE") sensors 30 of the exposed core variety can be formed by etching one or more walls of the configurations shown in FIGS. 14A and 14B. In these illustrative embodiments, a continuous length of sensor 30 has been exposed which will provide environmental sensitivity along the sensor length. Alternatively, portions of the sensor can be selectively exposed as desired in order to allow localized access to the core 31 of sensor 30.

As has been described, any single sensor configuration may have multiple detection sites that include different fluorescent materials that are designed for the detection of different entities. As an example, different channels or interaction regions of a sensor may be adapted to receive different materials. Additionally, a single channel or interaction region may have multiple different fluorescent materials located at different locations configured to detect multiple entities within a fluid that may be flushed through the channel or alternatively, in the example of an exposed core, where the core is exposed to the relevant material.

In another illustrative embodiment, the principles of optical time domain reflectometry (OTDR) may be employed to provide spatial information about the concentration of an entity within a material. In this illustrative embodiment, a sensor includes a plurality of detector sites made up of fluorescent material sensitive to the relevant entity which may be coated at specific locations at or near to the interface regions of high light intensity spaced along the elongate core.

As would be appreciated by those skilled in the art, when pulses of light are sent down the fiber there will usually be a background reflection component due to the back reflection of scattered light that occurs along the fiber. However, where one or more detection sites fluoresce as a result of detecting the relevant entity, then a pulse will result which can be measured over and above the background reflection component. The magnitude of this fluorescence pulse will depend on the backward fluorescence capture fraction which will differ from the forward fluorescence capture fraction discussed previously. In one example embodiment, sensor 200 may be used as a dip sensor wherein fluorescent emission coupled to the backward mode of propagation is detected in a similar setup to that depicted in FIG. 3 (i.e. for a filling length detector) except that an OSA is additionally coupled to the input end of sensor 200 for spectrum measurement of the captured fluorescence emission propagating in the backward mode.

In this manner, sensor 200 may be "dipped" into the relevant solution being tested which will cause the liquid to be drawn into channels 220, 221, 222 at the filling end by capillary action as has been discussed previously. It has been found that the backward fluorescence capture fraction is typically of higher efficiency than the forward fluorescence capture fraction and furthermore that there is no optimal length of the fiber that leads to maximal capture fraction but rather that the backward fluorescence capture function increases rapidly with the length of the fiber and then approaches an asymptotic value as opposed to decreasing (see for example, Afshar, V. S., Ruan, Y., Warren-Smith, S. C., Monro, T. M., "Enhanced fluorescence sensing using microstructured optical fibers: a comparison of forward and backward collection modes", Optics Letters, 33, 1473-1475 (2008) and Afshar, V. S., Ruan, Y., Warren-Smith, S. C., Ebendorf-Heidepriem, H., Monro, T. M., "Highly efficient fluorescence sensing using microstructured optical fibers; general model and experiment", 19th International Conference on Optical Fibre Sensors, Perth, Australia, Apr. 14-18, 2008 Proceedings of SPIE, 7004, 149 (2008), both of these publications hereby expressly incorporated by reference in their entirety).

As would be apparent to those skilled in the art, the use of the backward mode of propagation of the captured fluorescence emission and its associated increased efficiency will provide sensors of higher sensitivity that may be deployed in a dip sensing configuration that are able to respond in real time. Furthermore by measuring the time interval between the sending of a light pulse and the strong reflected fluorescence signal, the location along the fiber where the fluorescence occurred can be determined providing a one to one correspondence between the detection times and positions along the fiber.

In a further illustrative embodiment, a sensor in accordance with the present invention may be embodied in a fiber of suitable material having a solid core (e.g. of diameter of approximately 1 μm) which further incorporates a central air channel or hole (e.g. of diameter of approximately 100 nm), thereby providing an interaction region for the reception of a fluorescent material. In this embodiment, the interface region located between the core and the interaction region (in this case the air hole) will have an enhanced or higher intensity of light that is able to enhance the excitation of the fluorescent material.

In yet another illustrative embodiment, a sensor in accordance with the present invention may be directed towards the surface modes of an air-core photonic bandgap fiber where in the surface propagation mode the intensity of light is localized at the boundary or edge of the glass/material and air core interface. Accordingly, these regions may also form an interface region where the intensity of the guide light within the fiber may be intensified or enhanced to enhance the excitation of fluorescent material which in one example may be functionalized on this surface.

From a consideration of the various illustrative embodiments that are described herein, it can be concluded that the present invention provides a sensor that may be implemented in multiple configuration such as a point sensor, surface sensor or indeed a sensor able to receive liquids or fluids or a combination of these configurations. Furthermore, the sensor may be readily deployed and connected to standard fiber optical equipment as is known in the art.

Additionally, the recognition that particular combinations of core diameter and refractive index are capable of providing a region of enhanced or high intensity light available for excitation of a fluorescent material and subsequent efficient capture of fluorescent light in a fiber based sensor, allows for significantly sub-wavelength sensing regions to be realized, thereby providing a high degree of localisation for detection as well as substantially enhanced sensitivity when compared to prior art devices. As would be apparent to those skilled in the art, the present invention may be applied to any general waveguide configuration that includes a core region for guiding light and an associated interaction region that includes a florescent material.

Although illustrative embodiments of the present invention have been described in the foregoing detailed description, it will be understood that the invention is not limited to the embodiments disclosed, but is capable of numerous rearrangements, modifications and substitutions without departing from the scope of the invention as set forth and defined by the following claims.

The invention claimed is:

1. A sensor including:
   a micro structured optical fiber (MOF) including a solid core for propagating light having an excitation wavelength;
   an interaction region surrounding or part surrounding the solid core, the interaction region incorporating a fluorescent material for excitation by the propagated light to produce fluorescent light; and
   an interface region located between the solid core and the interaction region; wherein the solid core is adapted to increase a discontinuity in the electromagnetic field of the propagated light at the interface region, thereby enhancing the intensity of the propagated light at the interface region.

2. A sensor as claimed in claim 1, wherein the solid core is adapted to increase a discontinuity in the electromagnetic field of the propagated light at the interface region by having a cross sectional dimension less than or of the same order as the excitation wavelength.

3. A sensor as claimed in claim 1, wherein the solid core is adapted to increase a discontinuity in the electromagnetic field of the propagated light at the interface region by selecting the solid core to have a refractive index greater than that of the interaction region.

4. A sensor as claimed in claim 3, wherein a difference in refractive index between the solid core and the interaction region is greater than 0.3.

5. A sensor as claimed in claim 4, wherein the difference in refractive index between the solid core and the interaction region is greater than 0.6.

6. A sensor as claimed in claim 5, wherein the difference in refractive index between the solid core and the interaction region is greater than 1.0.

7. A sensor as claimed in claim 1, wherein the captured fluorescent light is propagated along the solid core.

8. A sensor as claimed in claim 1, wherein the interaction region extends longitudinally along the solid core.

9. A sensor as claimed in claim 1, wherein the solid core is a nanowire supported by a support structure that defines the interaction region.

10. A sensor as claimed in claim 9, wherein the support structure attaches the solid core to a supportive outer jacket.

11. A sensor as claimed in claim 1, wherein the intensity of the propagated light at the interface region is greater than an intensity of the propagated light within the solid core.

12. A sensor as claimed in claim 11, wherein the intensity of the propagated light at the interface region is greater than the intensity of a peak value of the propagated light within the solid core.

13. A sensor as claimed in claim 1, wherein the interaction region is a containment region for containing the fluorescent material in liquid form.

14. A sensor as claimed in claim 13, wherein the containment region is fillable from a filling end of the sensor.

15. A sensor as claimed in claim 14, wherein the sensor is irradiated with light having the excitation wavelength at an input end of the sensor, the input end opposed to the filling end, and wherein fluorescent light is captured and propagated back towards the input end for detection.

16. A sensor as claimed in claim 1, wherein the interface region is exposed to the environment along the solid core.

17. A sensor as claimed in claim 16, wherein the interface region is exposed to the environment at a plurality of locations along the solid core.

18. A sensor as claimed in claim 1, wherein the interface region includes at least one portion coated with the fluorescent material.

19. A sensor as claimed in claim 18, wherein the fluorescent material is a fluorescently labeled antibody for the detection of a predetermined biomolecule.

20. A sensor as claimed in claim 1, wherein the interface region is coated by a fluorescent material at a plurality of locations spaced along the solid core.

21. A sensor as claimed in claim 20, wherein a plurality of different fluorescent materials are coated at the plurality of locations along the solid core.

22. A sensor as claimed in claim 1, wherein the interface region is exposed along the solid core.

23. A sensor as claimed in claim 1, wherein the interface region is partially exposed at locations corresponding to the plurality of locations where the interface region is coated.

24. A method for sensing including:
   propagating light of an excitation wavelength down an solid core of a microstructured optical fibre (MOF) sensor, the sensor including an interaction region includes a fluorescent material;
   enhancing an intensity of the propagated light at an interface region relative to an intensity of the propagated light within the solid core by increasing a discontinuity in the electromagnetic field of the propagated light at the interface region, the interface region located between the solid core and the interaction region to thereby increase the amount of captured fluorescent light in the solid core.

25. A method for sensing as claimed in claim 24, wherein the intensity of the propagated light at the interface region is greater than a peak intensity of propagated light within the solid core.

26. A method for sensing as claimed in claim 24, wherein the step of enhancing includes reducing the cross sectional dimension of the solid core to less than or of the same order as the excitation wavelength.

27. A method for sensing as claimed in claim 24, wherein the step of enhancing includes selecting the solid core to have a refractive index substantially greater than that of the interaction region.

28. A method for sensing as claimed in claim 24, further including propagating the captured fluorescent light along the solid core.

29. A sensor including:
a microstructured optical fiber (MOF) including a plurality of solid cores for propagating light having an excitation wavelength;
a plurality of interaction regions surrounding or part surrounding a respective solid core and incorporating fluorescent material for excitation by the propagated light to produce fluorescent light; and
corresponding interface regions located between each of the interaction regions and the respective solid cores, wherein a selection of the plurality of solid cores are adapted to increase a discontinuity in the electromagnetic field of the propagated light at the corresponding interface region, thereby enhancing the intensity of the propagated light at the corresponding interface region.

30. A sensor as claimed in claim 29, wherein the fluorescent material is varied over the plurality of interaction regions.

* * * * *